US008959988B2

(12) United States Patent
Inagaki et al.

(10) Patent No.: US 8,959,988 B2
(45) Date of Patent: Feb. 24, 2015

(54) OXYGEN SENSOR CONTROL APPARATUS

(75) Inventors: Hiroshi Inagaki, Komaki (JP); Kentaro Mori, Nagoya (JP)

(73) Assignee: NGK Spark Plug Co., Ltd., Aichi (JP)

( * ) Notice: Subject to any disclaimer, the term of this patent is extended or adjusted under 35 U.S.C. 154(b) by 434 days.

(21) Appl. No.: 13/531,203

(22) Filed: Jun. 22, 2012

(65) Prior Publication Data

US 2012/0325662 A1 Dec. 27, 2012

(30) Foreign Application Priority Data

Jun. 24, 2011 (JP) ................................ 2011-141261

(51) Int. Cl.
*G01N 27/419* (2006.01)
*G01N 27/409* (2006.01)

(52) U.S. Cl.
CPC .................................... *G01N 27/409* (2013.01)
USPC ........................ 73/114.73; 73/23.31; 204/424

(58) Field of Classification Search
USPC .................. 73/114.71–114.73, 23.31–23.32; 205/784, 784.5; 204/424
See application file for complete search history.

(56) References Cited

U.S. PATENT DOCUMENTS

| 5,638,800 | A | 6/1997 | Furuya et al. |
| 7,367,330 | B2 | 5/2008 | Yoshidome |
| 2009/0082946 | A1 | 3/2009 | Ishizuka et al. |

FOREIGN PATENT DOCUMENTS

| JP | 1-216050 A | 8/1989 |
| JP | 2-169839 A | 6/1990 |
| JP | 4-292546 A | 10/1992 |
| JP | 8-158918 A | 6/1996 |
| JP | 2007-032466 A | 2/2007 |
| JP | 2008-298029 A | 12/2008 |
| JP | 2009-074435 A | 4/2009 |

OTHER PUBLICATIONS

JPO English language abstract of JP H01-216050 A, patent published Aug. 30, 1989.*
JPO computer-generated English language translation of JP H08-158918, patent published Jun. 18, 1996.*
JPO computer-generated English language translation of JP 2008-298029, patent published Dec. 11, 2008.*
Office Action mailed Apr. 1, 2014 in relevant Japanese Patent Application No. 2011-141261.

* cited by examiner

*Primary Examiner* — Alex Noguerola
(74) *Attorney, Agent, or Firm* — Sughrue Mion, PLLC

(57) ABSTRACT

In an oxygen sensor control apparatus, a CPU obtains a correction coefficient for calibrating the relation between output value of an oxygen sensor and oxygen concentration when a fuel cut operation is performed. When the amount of scavenging air (total supply amount of air) becomes equal to or greater than a predetermined amount in each fuel cut period, the CPU calculates an average output value Ipav from a plurality of output values (concentration corresponding values) Ipr of the oxygen sensor, from which values deviating from a predetermined range R1 have been removed. Subsequently, the CPU averages the values obtained in a plurality of fuel cut periods to thereby obtain a plural-time average output value Ipavf. The CPU obtains a correction coefficient for correcting the actual output value Ip of the oxygen sensor 20 on the basis of the Ipavf value and a previously set reference output value.

3 Claims, 6 Drawing Sheets

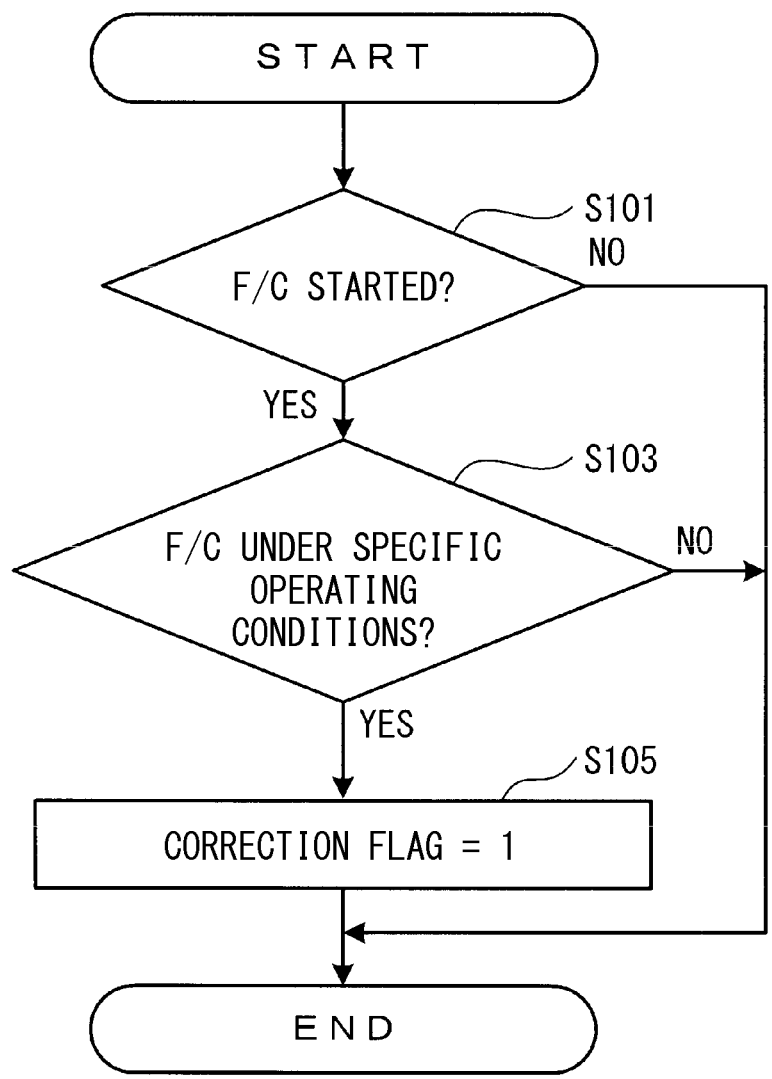

OXYGEN SENSOR CONTROL APPARATUS

BACKGROUND OF THE INVENTION

1. Field of the Invention

The present invention relates to an oxygen sensor control apparatus which calibrates the relation between the oxygen concentration of exhaust gas discharged from an internal combustion engine and the output of an oxygen sensor for detecting the oxygen concentration of the exhaust gas and which detects the oxygen concentration of the exhaust gas.

2. Description of the Related Art

Conventionally, an oxygen sensor has been disposed in an exhaust passage (exhaust pipe) of an internal combustion engine of an automobile or the like so as to detect the concentration of oxygen contained in exhaust gas for the purpose of controlling the air-fuel ratio of a fuel mixture supplied to the engine. Such an oxygen sensor includes, for example, a gas detection element which has at least one cell composed of an oxygen ion conductive zirconia substrate and a pair of electrodes formed thereon. However, such an oxygen sensor has a problem. That is, accuracy in detecting the oxygen concentration is inconsistent because of variation in output characteristics among individual oxygen sensors and deterioration of each oxygen sensor with time. In order to solve such a problem, a technique of performing atmospheric correction has been proposed; i.e., a technique of stopping supply of fuel to an internal combustion engine, and calibrating the relation between the output of the oxygen sensor and oxygen concentration when the exhaust passage is assumed to be substantially completely filled with atmospheric air (see, for example, Patent Document 1).

[Patent Document 1] Japanese Patent Application Laid-Open (kokai) No. 2007-32466 (paragraph 0040)

3. Problems to be Solved by the Invention:

However, the atmospheric correction method described in Patent Document 1 merely calculates a correction coefficient by comparing a reference output value Vstd which is output from a standard oxygen sensor in the atmospheric air and a current output value (i.e., a single output value) Vsen of an oxygen sensor in a fuel cut period during which the supply of fuel to the internal combustion engine is stopped. Even in such a fuel cut period, the output value of the oxygen sensor fluctuates because it pulsates as a result of operation of the internal combustion engine, and/or noise is superimposed on the output thereof. Therefore, the method of calculating the correction coefficient by merely comparing one output value of the oxygen sensor during a fuel cut period with the reference output value has a problem in that obtaining an accurate correction coefficient is difficult.

SUMMARY OF THE INVENTION

It is therefore an object of the present invention to provide an oxygen sensor control apparatus which can accurately calibrate the relation between the output of an oxygen sensor and the concentration of oxygen contained in exhaust gas, through use of an output value from the oxygen sensor obtained when a fuel cut operation is performed so as to stop the supply of fuel to an internal combustion engine.

The above object has been achieved by providing an oxygen sensor control apparatus (1) of the invention which obtains a correction coefficient when a fuel cut operation is performed so as to stop the supply of fuel to an internal combustion engine, the correction coefficient being used to calibrate the relation between an actual output value of an oxygen sensor attached to an exhaust pipe of the internal combustion engine and the oxygen concentration, and which detects the oxygen concentration of the exhaust gas through use of the actual output value and the correction coefficient. The oxygen sensor control apparatus comprises average output value calculation means for calculating an average output value by averaging a plurality of actual output values of the oxygen sensor acquired in each period in which the fuel cut operation is performed once or by averaging concentration corresponding values calculated from the actual output values and representing the oxygen concentration acquired in each period in which the fuel cut operation is performed once; plural-time average output value calculation means for calculating a plural-time average output value for performance of the fuel cut operation in a predetermined number of times equal or greater than two times, by averaging a plurality of the average output values each calculated for each performance of the fuel cut operation; correction coefficient calculation means for obtaining a new correction coefficient on the basis of the plural-time average output value and a reference output value set in advance, the new correction coefficient being used for correcting the actual output value of the oxygen sensor; total supply amount calculation means for acquiring, from supply amount measurement means for measuring the amount of air supplied from the internal combustion engine to the exhaust pipe, the amount of air supplied to the exhaust pipe, and for calculating a total supply amount, which is the total amount of air supplied to the exhaust pipe during each period in which the fuel cut operation is performed once; and total supply amount determination means for determining, in each period in which the fuel cut operation is performed once, whether or not the total supply amount calculated by the total supply amount calculation means becomes equal to or greater than a predetermined amount set in advance, wherein the average output value calculation means calculates the average output value from a plurality of the actual output values of the oxygen sensor or the concentration corresponding values acquired at predetermined time intervals after the total supply amount determination means determines that the total supply amount from the start of the fuel cut operation becomes equal to or greater than the predetermined amount.

In general, even when the fuel cut operation of stopping the supply of fuel to the internal combustion engine is performed, the output (output waveform) of the oxygen sensor may pulsate as a result of operation of the internal combustion engine at the time of the fuel cut or the actual output value output from the oxygen sensor may contain noise. In view of the above, in the present invention, the average output value is calculated from a plurality of actual output values of the oxygen sensor acquired in a single period of the fuel cut operation or concentration corresponding values calculated from the actual output values and representing the oxygen concentration acquired in a single period of the fuel cut operation. Thus, the influence of noise and/or pulsation of the output waveform of the oxygen sensor is eliminated or mitigated. Also, even when the fuel cut operation of stopping the supply of fuel to the internal combustion engine is performed, the operating conditions just before the fuel cut involve some variations (deviations). In view thereof, in the present invention, a plural-time average output value for performance of the fuel cut operation in a predetermined number of times equal to or greater than two times is calculated by averaging a plurality of the average output values each calculated for each performance of the fuel cut operation, and a new correction coefficient used for correcting the actual output value of the oxygen sensor is obtained on the basis of the plural-time average output value and a reference output value set in advance. Therefore, according to the oxygen sensor control apparatus of the present invention, an accurate correction coefficient can be calculated.

Moreover, the average output value is calculated from the actual output values of the oxygen sensor or the concentration corresponding values when the amount of air supplied to the exhaust pipe from the start of the fuel cut operation (each fuel cut operation) becomes equal to or greater than a predetermined amount set in advance. Therefore, the average output value can be calculated after the start of the fuel cut operation in a state in which the output waveform of the oxygen sensor does not change greatly and is relatively stable, whereby an accurate correction coefficient can be calculated.

Notably, in the present embodiment, the "concentration corresponding values calculated from the actual output values and representing the oxygen concentration" may be values obtained by multiplying the individual actual output values of the oxygen sensor by the current correction coefficient set in the oxygen sensor control apparatus (when a new correction coefficient is obtained, by the new correction coefficient). Alternatively, the concentration corresponding values may be amplified values obtained by amplifying the actual output values with a predetermined multiplying factor or values obtained by multiplying the amplified values by the above-mentioned correction coefficient.

In a preferred embodiment (2) of the oxygen sensor control apparatus (1) above, the average output value calculation means is configured to remove values deviating from a first range from a plurality of actual output values of the oxygen sensor acquired in each period in which the fuel cut operation is performed once or from the concentration corresponding values calculated from the actual output values and representing the oxygen concentration acquired in each period in which the fuel cut operation is performed once, and is configured to calculate the average output value by averaging the remaining values.

By means of calculating the average output value by averaging the actual output values or the concentration corresponding values while removing therefrom values deviating from the predetermined first range, even in the case where large or small actual output values or concentration corresponding values are unexpectedly obtained as a result of the influence of pulsation or noise, it is possible to calculate the average output value while removing these values. Thus, a more accurate correction coefficient can be calculated.

In the oxygen sensor control apparatus of the present invention, the plural-time average output value calculation means is configured to remove values deviating from a predetermined second range, which is narrower than the first range, from a plurality of the average output values, and to calculate the plural-time average output value by averaging the remaining average output values.

By means of applying the second range narrower than the first range to the average output values obtained by averaging the values within the first range so as to remove or mitigate the influence of pulsation or noise, it becomes possible to calculate the plural-time average output value while removing the average output values containing errors. Thus, a more stable correction coefficient can be calculated.

Moreover, in a preferred embodiment (3) of the oxygen sensor control apparatus (2) above, the first range is set around the reference output value such that the center of the first range coincides with the reference output value. By setting the first range around the reference output value such that the center of the first range coincides with the reference output value, the influence of noise or pulsation of the output waveform of the oxygen sensor during the fuel cut period can be eliminated or mitigated effectively, whereby a more stable correction coefficient can be obtained.

Effect of the Invention

According to the present invention, the average output value is calculated on the basis of the actual output values from the oxygen sensor or the concentration corresponding values obtained when a fuel cut operation is performed so as to stop the supply of fuel to the internal combustion engine, and the correction coefficient is calculated using the plural-time average output value calculated from the average output value. Therefore, it is possible to obtain a correction coefficient which allows accurate calibration of the relation between the output of the oxygen sensor and the oxygen concentration of exhaust gas. Thus, the detection accuracy of the oxygen sensor can be maintained at a satisfactory level over a long period of time.

BRIEF DESCRIPTION OF THE DRAWINGS

FIG. 6 is a flowchart showing a determination processing of determining whether to perform atmospheric correction processing.

DESCRIPTION OF REFERENCE NUMERALS

Figure 1:
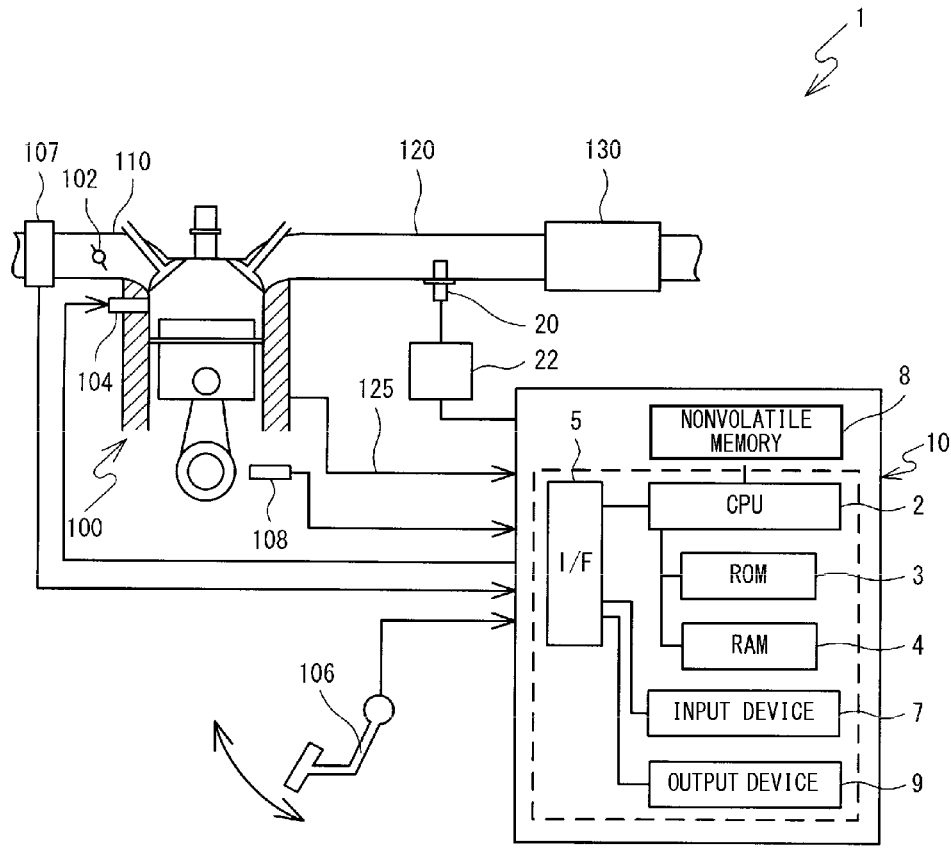
FIG. 1 is a diagram showing the configuration of an engine control system 1 including an oxygen sensor control apparatus 10 according to an embodiment of the present invention.

Reference numerals used to identify various features in the drawings include the following.
2: CPU
3: ROM
4: RAM
8: nonvolatile memory
10: oxygen sensor control apparatus (ECU)
20: mounted oxygen sensor (oxygen sensor)
100: internal combustion engine
Kp, Kq: correction coefficient
Ipso: reference oxygen output value
Ipro: output value when the oxygen sensor is exposed to an atmosphere whose oxygen concentration is substantially the same as that of a specific atmosphere Ipsf: fuel-cut reference output value (reference output value)
Ipr: value (concentration corresponding value) obtained by multiplying the actual output value of the mounted oxygen sensor by the correction coefficient Kp
Ipav: average output value
Ipavf: plural-time average output value
R1: first range
R2: second range
R3: third range
M1: total supply amount of air (amount of scavenging air)
M2: predetermined amount

DETAILED DESCRIPTION OF THE PREFERRED EMBODIMENTS

An embodiment of the present invention will now be described with reference to the drawings. Notably, the drawings are used for describing the technical features which can be employed by the present invention. The configuration of an apparatus, the flowcharts of various processing, etc., shown in the drawings are mere examples, and the present invention should not be construed as being limited thereto.

FIG. 1 is a diagram showing the configuration of an engine control system 1 including an oxygen sensor control apparatus 10. In the engine control system 1, an oxygen sensor 20 is mounted to an exhaust pipe 120 of an internal combustion engine 100 of a vehicle (hereinafter, the oxygen sensor 20 will be referred to as the "mounted oxygen sensor 20"), and a controller 22 is connected to the mounted oxygen sensor 20. The oxygen sensor control apparatus 10 is connected to the controller 22. The oxygen sensor control apparatus 10 according to the present embodiment functions as an engine control unit (ECU).

A throttle valve 102 is provided in an intake pipe 110 of the internal combustion engine 100, and an injector (fuel injection valve) 104 is disposed on each cylinder of the internal combustion engine 100 so as to supply fuel into the cylinder. An exhaust gas purification catalyst 130 is attached to a downstream portion of the exhaust pipe 120. Various sensors, such as a pressure sensor (not shown), a temperature sensor (not shown), and a crank angle sensor 108, are attached to the internal combustion engine 100. An air-flow meter 107 is disposed in the intake pipe 110. The air-flow meter 107 measures the intake amount of air. Since the intake air is supplied to the exhaust pipe 120, the air-flow meter 107 measures the amount of air supplied to the exhaust pipe 120 by measuring the amount of intake air.

Operating condition information (engine pressure, temperature, crank angle, and engine rotational speed, air supply amount, etc.) from the various sensors and the air-flow meter 107 is fed to the oxygen sensor control apparatus 10. Notably, an arrow 125 in FIG. 1 represents a path through which the engine pressure and the temperature, which are part of the operating condition information, are input to the oxygen sensor control apparatus 10. The oxygen sensor control apparatus 10 controls the throttle valve 102 to thereby control the amount of air supplied to the internal combustion engine 100 and controls the amount of fuel injected from the injector 104, in accordance with the above-mentioned operating condition information, the oxygen concentration of exhaust gas detected by the mounted oxygen sensor 20, the amount by which an accelerator pedal 106 is depressed by a driver, etc. Thus, the oxygen sensor control apparatus 10 operates the internal combustion engine 100 at a proper air-fuel ratio.

The ECU 10 is a unit in which a microcomputer and a nonvolatile memory 8 such as EEPROM are mounted on a circuit board. The microcomputer includes a central processing unit (CPU) 2, ROM 3, RAM 4, an interface circuit (I/F) 5 for external devices, an input device 7 for inputting data from the outside, and an output device 9 for outputting data to the outside. The ECU 10 (CPU 2) processes an input signal in accordance with a program stored in the ROM 3 in advance and outputs from the output device 9 a control signal for controlling the amount of fuel injected by the injector 104. The ECU 10 also performs atmospheric correction processing which will be described below.

The mounted oxygen sensor 20 may be a so-called two-cell-type air-fuel-ratio sensor which includes two cells each composed of an oxygen-ion conductive solid electrolyte substrate and a pair of electrodes provided thereon. Specifically, the air-fuel-ratio sensor may be composed of a gas detection element and a housing which holds the gas detection element therein and which is attached to the exhaust pipe 120. The gas detection element includes an oxygen pump cell and an oxygen concentration detection cell, which are stacked together with a hollow measurement chamber formed therebetween. Exhaust gas is introduced into the measurement chamber via a porous member. Further, a heater is stacked on the two cells so as to heat these cells to an activation temperature. Notably, in order to distinguish the oxygen sensor 20 actually mounted onto an individual internal combustion engine from a reference oxygen sensor to be described later, in the present invention, the oxygen sensor 20 mounted onto the engine will be referred to as the "mounted oxygen sensor."

The mounted oxygen sensor 20 is connected to the controller 22, which is a well-known detection circuit including various resistors, differential amplifiers, etc. The controller 22 supplies pump current to the mounted oxygen sensor 20, converts the pump current to a voltage, and outputs the voltage to the ECU 10 as an oxygen concentration detection signal. More specifically, the controller 22 controls the supply of electricity to the oxygen pump cell such that the output of the oxygen concentration detection cell becomes constant. The oxygen pump cell pumps oxygen within the measurement chamber to the outside, or pumps oxygen into the measurement chamber. At that time, a pump current flows through the oxygen pump cell. The controller 22 coverts this pump current to voltage via a detection resistor, and outputs the voltage to the ECU 10.

Next, an atmospheric correction method (a method of calculating a correction coefficient) for the mounted oxygen sensor 20 will be described. Atmospheric correction is the processing of calculating a correction coefficient for calibrating the relation between the output (actual output value) of the mounted oxygen sensor 20 attached to the internal combustion engine 100 and oxygen concentration, when a fuel cut operation (hereinafter referred to as "F/C") is performed so as to stop the supply of fuel to the internal combustion engine 100 under specific operating conditions. The atmospheric correction is performed by calculating a correction coefficient which eliminates the deviation of the output characteristic of the mounted oxygen sensor 20 attached to the internal combustion engine 100 from the output characteristic of a predetermined ideal oxygen sensor; i.e., a standard oxygen sensor which has the same structure as that of the mounted oxygen sensor 20 and an output characteristic at the center of a range of manufacturing variation thereof (hereinafter referred to as a "reference oxygen sensor"). The actual output value of the mounted oxygen sensor 20; i.e., the value actually output from the mounted oxygen sensor 20 when the internal combustion engine is operating, is corrected through use of the obtained correction coefficient.

No limitation is imposed on the value of the correction coefficient, insofar as the correction coefficient can eliminate the deviation between the output characteristic of the reference oxygen sensor and the output characteristic of the mounted oxygen sensor 20. For example, the following correction coefficient Kp can be used. That is, in the present embodiment, in order to enable the atmospheric correction to be performed when the internal combustion engine 100 is operating, a value (the correction coefficient Kp) obtained by dividing a reference oxygen output value Ipso, which is a value output from the reference oxygen sensor when it is exposed to a specific atmosphere having a known oxygen concentration, by an output value Ipro, which is a value output from the mounted oxygen sensor 20 when it is exposed to an atmosphere having an oxygen concentration substantially the same as that of the specific atmosphere, is stored in the nonvolatile memory 8 of the ECU 10 as a correction coefficient in advance. An example of the "specific atmosphere which has a known oxygen concentration" is the ambient atmosphere (air whose oxygen concentration is about 20.5%); however, the specific atmosphere may be an oxygen atmosphere whose oxygen concentration differs from that of the ambient atmosphere. When the reference oxygen sensor is exposed to the above-mentioned "specific atmosphere having a known oxygen concentration," the reference oxygen sensor may be attached to a predetermined measurement system so that the reference oxygen sensor is exposed to that atmosphere (e.g., the ambient atmosphere).

Meanwhile, the "atmosphere which has an oxygen concentration substantially the same as that of the specific atmosphere" and to which the mounted oxygen sensor 20 is exposed may be the same oxygen atmosphere as the atmosphere to which the reference oxygen sensor is exposed or an atmosphere whose oxygen concentration deviates from that of the oxygen atmosphere to which the reference oxygen sensor is exposed, so long as the deviation falls within a range of ±5.0% (more preferably, ±1.0%). When the mounted oxygen sensor 20 is exposed to the above-mentioned "atmosphere which has an oxygen concentration substantially the same as that of the specific atmosphere," as in the case of the reference sensor, the mounted oxygen sensor 20 may be attached to a predetermined measurement system so that the reference oxygen sensor is exposed to that atmosphere (e.g., the ambient atmosphere). Alternatively, the mounted oxygen sensor 20 may be attached to the exhaust pipe 120 of the actual internal combustion engine 100, and a gas which forms the above-mentioned oxygen atmosphere may be passed through the exhaust pipe 120, whereby the mounted oxygen sensor 20 is exposed to that atmosphere.

Figure 2:
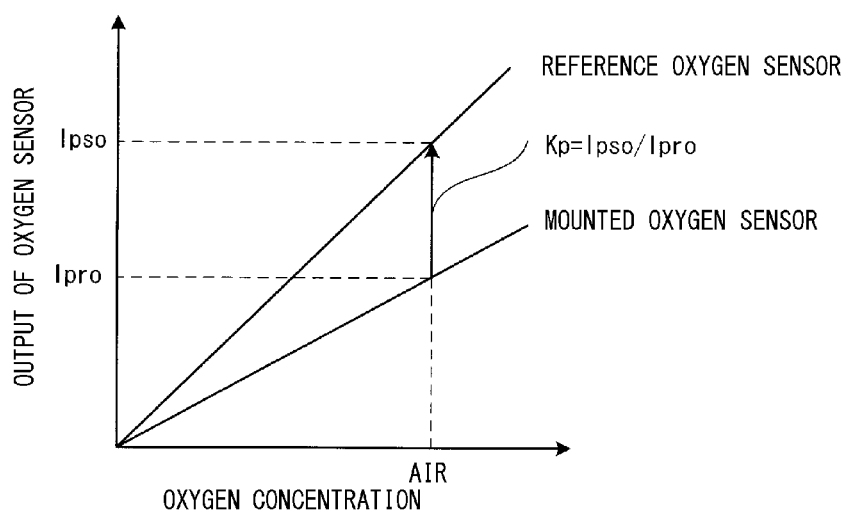
FIG. 2 is a chart showing a method for obtaining a correction coefficient Kp in advance.

When a new correction coefficient Kq (which will be described later) is obtained as a result of execution of atmospheric correction processing while the internal combustion engine 100 is operating, the correction coefficient Kq is stored as a new correction coefficient Kp for update. However, in the present embodiment, before the shipment of the internal combustion engine 100, an initial correction coefficient Kp is stored in the nonvolatile memory 8 by the following procedure. Specifically, a reference oxygen sensor is attached to a predetermined measurement system so as to be exposed to the ambient atmosphere (air), and a reference oxygen output value Ipso is obtained as shown in FIG. 2. Subsequently, the mounted oxygen sensor 20 is attached to the exhaust pipe 120 of the internal combustion engine 100 before shipment (more specifically, at the time of shipment inspection), the internal combustion engine 100 is operated, and the oxygen concentration of the gas flowing through the exhaust pipe is rendered substantially the same as that of the atmospheric air by fully opening the throttle valve in a state in which the supply of fuel is stopped or in which the fuel-supply-stopped state is maintained for a long period of time. The output value Ipro output from the mounted oxygen sensor 20 at that time is detected (see FIG. 2).

Subsequently, as shown in FIG. 2, the correction coefficient Kp is calculated by a formula (the reference oxygen output value Ipso)/(the output value Ipro of the mounted oxygen sensor 20); i.e., by dividing the reference oxygen output value Ipso by the output value Ipro of the mounted oxygen sensor 20 placed under the atmosphere having the same oxygen concentration. This correction coefficient Kp is stored in the nonvolatile memory 8. The correction coefficient Kp stored in the nonvolatile memory 8 as an initial value as described above is used as a correction coefficient for correcting the actual output value Ip of the mounted oxygen sensor 20 until the next update of the correction coefficient (overwriting of the correction coefficient) is performed.

Figure 3:
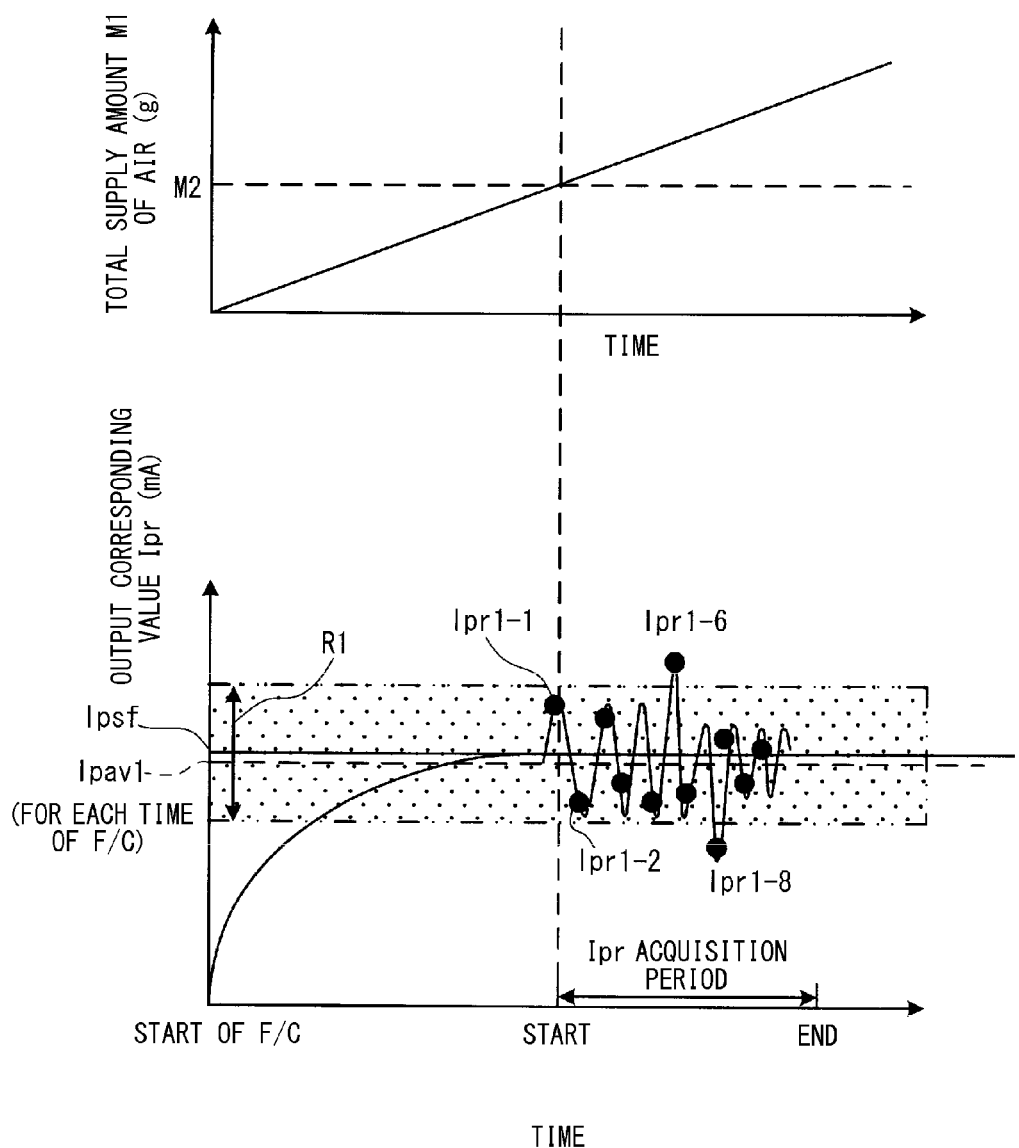
FIG. 3 is a chart showing a change in the total supply amount M1 of air during a fuel cut period, a change in an output value Ipr of a mounted oxygen sensor 20, and a method for averaging a value Ipr obtained by multiplying the actual output value of the mounted oxygen sensor 20 by the correction coefficient Kp.

Next, an example change in the output value Ipr of the mounted oxygen sensor 20 during a single fuel cut period will be described with reference to FIG. 3. FIG. 3 shows the relation between the time elapsed after start of a fuel cut operation and the total supply amount M1 of air (a graph on the upper side of the sheet), and the relation between the time elapsed after start of the fuel cut operation and the output value Ipr of the mounted oxygen sensor 20 (a graph on the lower side of the sheet). The total supply amount M1 of air is obtained through cumulative addition (integration) of the amount of air supplied to the exhaust pipe 120 measured by the air-flow meter 107 during the fuel cut period. The total supply amount M1 of air increases with the time that has elapsed after the start of the fuel cut operation. Since air is supplied to the exhaust pipe 120, the exhaust gas discharged before the start of the fuel cut operation and remaining in the exhaust pipe 120, etc., is replaced with air.

Since some time is required for the air to replace the exhaust gas remaining in the exhaust pipe 120, etc., some time is needed for the oxygen concentration within the exhaust pipe 120 to approach the oxygen concentration of air. FIG. 3 shows an example case where the oxygen concentration within the exhaust pipe 120 is determined to have approached the oxygen concentration of air, when the total supply amount M1 of air reaches a predetermined amount M2 (g) (e.g., 50 g). The timing at which the total supply amount M1 of air reaches the predetermined amount M2 (g) is the timing at which an Ipr acquisition period shown in FIG. 3 starts. The output value Ipr of the mounted oxygen sensor 20 gradually increases until the total supply amount M1 of air reaches the predetermined amount M2 (g). When the oxygen concentration within the exhaust pipe 120 approaches the oxygen concentration of air, the output value Ipr generally becomes stable. However, even after the oxygen concentration within the exhaust pipe 120 has approached the oxygen concentration of air, the output value Ipr pulsates because piston motion is repeated in each of the cylinders of the internal combustion engine 100. Notably, in actuality, the output value Ipr gradually increases while pulsating during a period between the start of F/C and the start of the Ipr acquisition period shown in FIG. 3. However, this pulsation is not illustrated in FIG. 3.

Next, in the present embodiment, a fuel-cut reference output value Ipsf is stored in the nonvolatile memory 8 (EEPROM) of the ECU 10 as a reference output value. Ipsf is compared with the actual output value of the mounted oxygen sensor 20 when the internal combustion engine 100 having the mounted oxygen sensor 20 attached thereto is in the fuel cut period. This fuel-cut reference output value Ipsf is also stored in the nonvolatile memory 8 before shipment of the internal combustion engine 100. In the present embodiment, the fuel-cut reference output value Ipsf is obtained by intentionally performing the F/C in a state in which the mounted oxygen sensor 20 is attached to the exhaust pipe 120 of the internal combustion engine 100 after the correction coefficient Kp is calculated in the above-described procedure. Specifically, at the time of shipment inspection of the internal combustion engine 100, operation of the internal combustion engine 100 is started in a state in which the mounted oxygen sensor 20 for which the correction coefficient Kp has been obtained as described above is attached to the exhaust pipe 120 of the internal combustion engine 100. Subsequently, the F/C is performed manually or mechanically in a certain operation state, and the actual output value of the mounted oxygen sensor 20 is obtained at predetermined intervals after a point in time when the gas discharged from the cylinders after start of the F/C is expected to have reached an area around the mounted oxygen sensor 20 (for example when the total supply amount M1 of air after start of the F/C reaches the predetermined amount M2 (g) (e.g., 50 g)). A plurality of values obtained by multiplying the obtained actual output values by the correction coefficient Kp are averaged so as to obtain the fuel-cut reference output value Ipsf. The fuel-cut reference output value Ipsf obtained in this manner is stored in the nonvolatile memory 8. Notably, the fuel-cut reference output value Ipsf corresponds to the "reference output value" of the invention.

Notably, in the case of the internal combustion engine 100, in accordance with operating conditions, such as deceleration of the vehicle and the amount of intake air, the ECU 10 outputs an instruction to reduce the amount of fuel injected from the injector 104 to zero. Therefore, the determination as to whether the F/C has been started can be made through detection of the instruction. Incidentally, there are various combinations of operating conditions under which the F/C may be started. However, if the specific operating conditions under which the F/C is started during the shipment inspection of the internal combustion engine 100 (in order to calculate the above-mentioned fuel-cut reference output value Ipsf) differ from those under which the F/C is started when the vehicle (the internal combustion engine 100) travels (operates) after the shipment thereof so as to perform atmospheric correction processing described below, the atmospheric correction processing cannot be performed under the same conditions. Consequently, the accuracy of the atmospheric correction (i.e., the accuracy in calculating an average output value Ipav, a plural-time average output value Ipavf, and a correction coefficient Kq, which will be described later) is reduced. Accordingly, in the present embodiment, the calculation of the average output value Ipav, the plural-time average output value Ipavf, the fuel-cut reference output value Ipsf, and the processing of calculating the correction coefficient Kq described below are performed only for a fuel cut operation performed under a predetermined condition in which the engine is operated under predetermined operating conditions.

However, it is not necessarily required to perform the fuel cut operation under the same or fixed conditions, and the following procedure may be employed. The actual output value Ip of the mounted oxygen sensor 20 is obtained in a plurality of fuel cut operations performed under different conditions, and the average output value Ipav, the plural-time average output value Ipavf, the fuel-cut reference output value Ipsf, the correction coefficient Kq, etc., are calculated on the basis of the obtained actual output value Ip. Notably, determination as to whether or not the F/C has been started under specific operating conditions during operation of the internal combustion engine 100 can be made by use of at least one of parameters representing the operation state of the internal combustion engine (e.g., engine rotational speed, engine load, and intake air amount) just before the F/C starts (just before the F/C is determined to have started). Specifically, when the at least one parameter satisfies a predetermined condition (i.e., a predetermined condition previously set so as to obtain the fuel-cut reference output value Ipsf), the F/C is determined to have been started under a predetermined condition (under the operating conditions determined in advance).

Figure 7A:
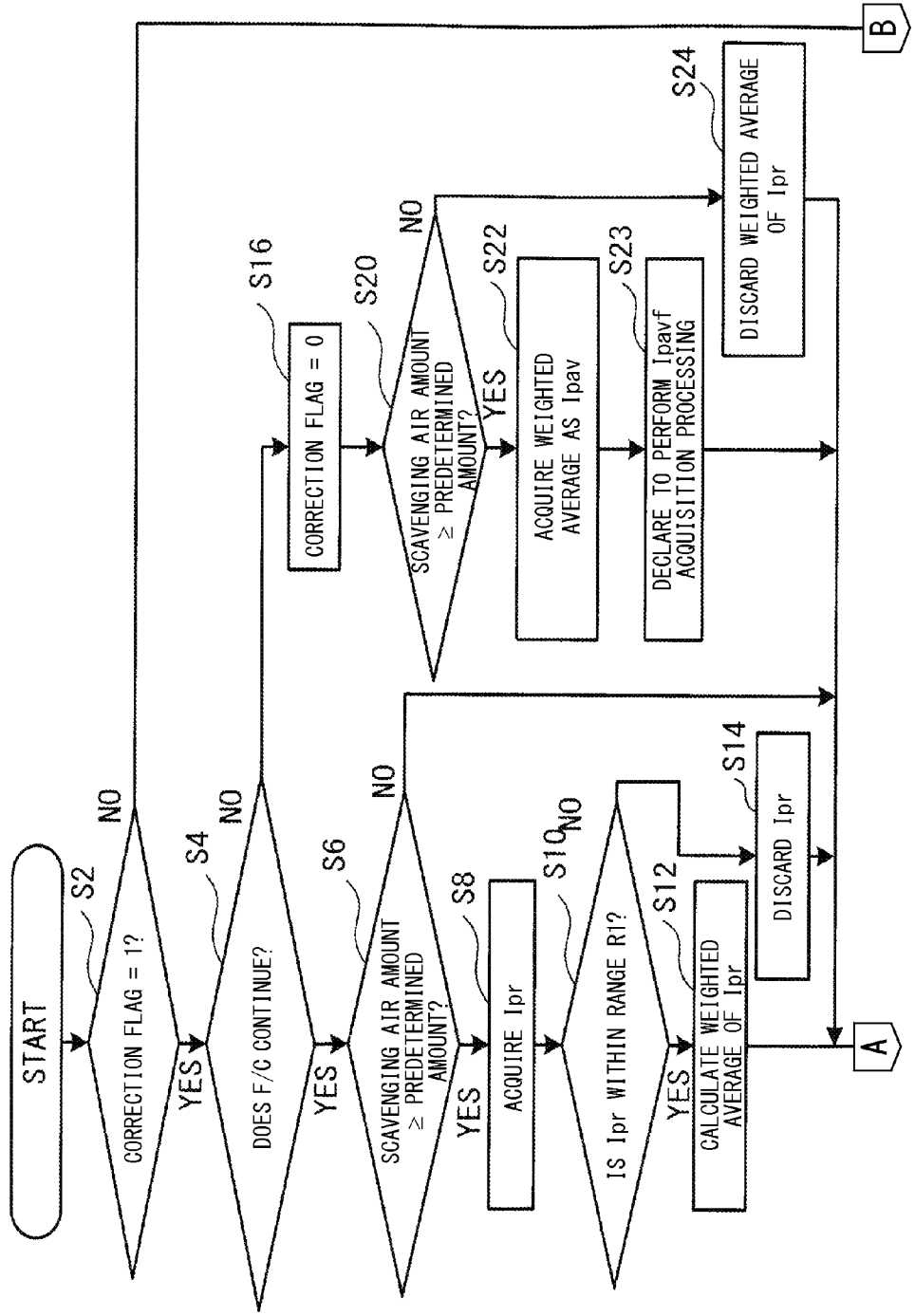
FIGS. 7A and 7B are flowcharts showing the atmospheric correction processing of calculating a correction coefficient Kq on the basis of the value Ipr obtained by multiplying the actual output value of the mounted oxygen sensor 20 by the correction coefficient Kp, and storing it as a new correction coefficient Kp for update.
Figure 7B:
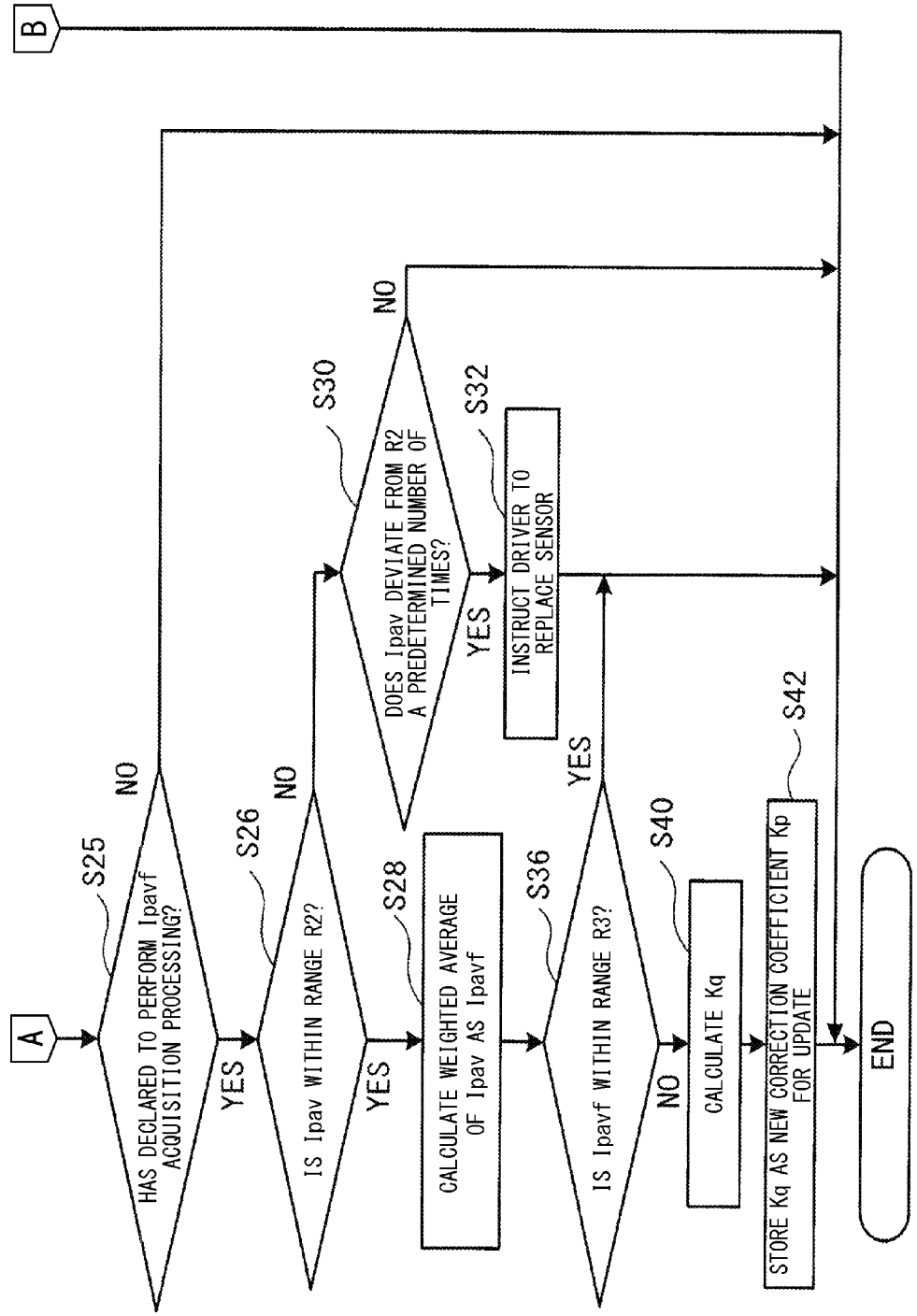

Next, with reference to the flowcharts shown in FIGS. 6 and 7, the outline of the atmospheric correction processing which is executed by the CPU 2 of the ECU 10 when the vehicle is traveling (when the internal combustion engine 100 is operating) will be described. The atmospheric correction processing is executed by use of the average output value Ipav and the plural-time average output value Ipavf in a state in which the correction coefficient Kp and the fuel-cut reference output value Ipsf are stored in the nonvolatile memory 8. Notably, FIG. 6 is a flowchart showing the processing (program) of determining whether to perform the atmospheric correction processing. FIGS. 7A and 7B are flowcharts showing the atmospheric correction processing (program) of calculating the correction coefficient Kq by use of the average output value Ipav and the plural-time average output value Ipavf. After the ECU 10 is powered, the programs represented by the two flowcharts are repeatedly executed at predetermined intervals (e.g., 1 msec).

First, the processing of determining whether to perform the atmospheric correction processing will be described with reference to FIG. 6. The CPU 2 determines whether or not the F/C has been started when the internal combustion engine 100 is being operated (S101). As described above, this determination is made by determining whether or not the instruction for reducing the amount of fuel injected from the injector 104 to zero has been output. When that instruction is output, the CPU 2 determines that the F/C has been started (S101: YES). Subsequently, the CPU 2 determines whether or not the F/C is performed under the specific operating conditions (S103). As described above, this determination is made by determining whether or not at least one of parameters representing the operation state of the internal combustion engine (e.g., engine rotational speed, engine load, and intake air amount) just before the F/C starts (just before the F/C is determined to have started) satisfies a predetermined condition. In the case where the CPU 2 determines that the F/C is performed under the specific operating conditions (S103: YES), the CPU 2 sets the value of a correction flag to "1" (S105). Notably, when the ECU 100 is powered, the value of the correction flag is set to "0." Meanwhile, in the case where the result of the determination in S101 is NO and the result of the determination in S103 is NO, the CPU 2 ends the present processing. After that, the CPU 2 repeatedly executes the present processing from the beginning (S101: YES). Notably, in the case where the CPU 2 determines in S101 that the F/C has been started (S101), in parallel with the above-described processing, the CPU 2 sets the total supply amount M1 (the total amount of air supplied to the exhaust pipe 120 during the fuel cut period) to "0." Notably, the total supply amount M1 is stored in the RAM 4. Subsequently, the CPU 2 obtains the air supply amount from the air-flow meter 107 and starts the cumulative calculation of the total supply amount M1.

Next, the atmospheric correction processing will be described with reference to the flowchart shown in FIGS. 7A and 7B. First, in step S2, the CPU 2 determines whether or not the value of the correction flag is "1." In the case where the value of the correction flag is "1" (S2: YES), the CPU 2 proceeds to step S4. This determination is made on the basis of the correction flag which has been set to "1" in step S105 of FIG. 6 and stored in the RAM 4. Meanwhile, in the case where the value of the correction flag is not "1" (S2: NO), the CPU 2 ends the present processing. In the case where the result of the determination in S2 is YES, the CPU 2 determines whether or not the F/C continues (S4). In the case where the F/C continues (S4: YES), the CPU 2 proceeds to S6 for determination processing.

Next, in the determination processing of S6, the CPU 2 determines whether or not the cumulative amount of scavenging air (the total supply amount M1 of air) in a single fuel cut period becomes equal to or greater than the predetermined amount M2 (e.g., 50 g) (S6). Notably, the value of the predetermined amount M2 is stored in the nonvolatile memory 8. In the case where the total supply amount M1 is not equal to or greater than the predetermined amount M2 (S6: NO), the CPU 2 proceeds to S25. Since the CPU 2 has not yet declared to execute Ipavf acquisition processing (S25: NO), the CPU 2 ends the processing. Subsequently, the determination in S6 is repeatedly performed at predetermined intervals (e.g., 1 msec).

The reason for waiting until the amount of scavenging air (the total supply amount M1 of air) becomes equal to or greater than the predetermined amount M2 (e.g., 50 g) is as follows. Even after the F/C is started, the combustion gas produced before the start of the F/C remains in the exhaust pipe 120, etc., and scavenging air of the predetermined amount M2 is needed so as to make the composition of the combustion gas similar to that of new gas (air) or to replace the combustion gas with the new gas (air). Thus, the oxygen concentration within the exhaust pipe 120 approaches the oxygen concentration of air with some delay. Therefore, the actual output value (output waveform) of the mounted oxygen sensor 20 also increases gradually with the increasing oxygen concentration within the exhaust pipe 120 after the start of the F/C, and, when the oxygen concentration of the gas within the exhaust pipe 120 becomes substantially the same as that of air, the actual output value assumes a generally stable value although the output waveform pulsates. In view of this, in step S6, the CPU 2 determines whether or not the F/C which has been started under the specific operating conditions continues until the scavenging air (M2) is supplied. Also, the oxygen concentration of the gas within the exhaust pipe 120 is expected to become substantially the same as that of air or the gas within the exhaust pipe 120 is expected to be replaced with air.

Returning to FIGS. 7A and 7B, when the amount of scavenging air (the total supply amount M1) becomes equal to or greater than the predetermined amount M2 (e.g., 50 g) (S6: YES), the CPU 2 acquires the output corresponding value Ipr of the mounted oxygen sensor 20 and stores it in the RAM 4 (S8). Notably, the output corresponding value Ipr is repeatedly obtained at predetermined intervals (e.g., 1 msec) so long as the F/C under the specific operating conditions continues. The output corresponding value Ipr is obtained by multiplying the actual output value Ip output from the mounted oxygen sensor 20 by the current correction coefficient Kp stored in the nonvolatile memory 8. That is, the output corresponding values Ipr, which are values obtained by multiplying the actual output values Ip by the current correction coefficient Kp, correspond to the "concentration corresponding values calculated from the actual output values and representing the oxygen concentration" of the invention.

Next, the CPU 2 determines whether or not the output corresponding value Ipr acquired in S8 falls within a predetermined first range R1 (S10). In the case where the output corresponding value Ipr falls within the predetermined first range R1 (S10: YES), the CPU 2 calculates the weighted average of the output corresponding values Ipr (S12). Meanwhile, in the case where the output corresponding value Ipr does not fall within the predetermined first range R1 (S10: NO), the CPU 2 performs discarding processing for deleting the output corresponding value Ipr acquired in S8 and stored in RAM 4 (S14).

In general, even when the F/C is started under the predetermined condition in which the engine is operated under the predetermined operating conditions, the individual actual output value Ip of the mounted oxygen sensor 20 (therefore, the individual output corresponding value Ipr) may pulsate, or contain noise accidentally. In view of this, in the present embodiment, by calculating the average output value Ipav by averaging a plurality of output corresponding values Ipr acquired in a single fuel cut period, the influence of the pulsation and noise is eliminated or mitigated, whereby a stable value representing the output of the mounted oxygen sensor 20 in a single F/C is obtained. Specifically, as shown in FIG. 3, of the values (Ipr1-1, Ipr1-2, etc.) obtained by multiplying the individual actual output values Ip obtained in a single fuel cut period by the present correction coefficient Kp, only the values within the predetermined first range R1 (i.e., only the values of the output corresponding value Ipr for which the CPU 2 makes a "YES" determination in S10) are acquired so as to calculate the average output value Ipav (S12). Notably, in the present embodiment, the upper and lower limits of the range R1 shown in FIG. 3 are determined on the basis of the fuel-cut reference output value Ipsf and a predetermined variation range. For example, the upper limit is set to a value obtained by adding 7.5% of the fuel-cut reference output value Ipsf to the fuel-cut reference output value Ipsf (center value), and the lower limit is set to a value obtained by subtracting 7.5% of the fuel-cut reference output value Ipsf from the fuel-cut reference output value Ipsf (center value).

As shown in FIG. 3, of the values Ipr1 obtained by multiplying the actual output values Ip obtained in a single fuel cut period by the correction coefficient Kp, the two values Ipr1-1 and Ipr1-2 deviate to the increasing and decreasing sides, respectively, in relation to the reference output value Ipsf (the output of the mounted oxygen sensor 20 pulsate). However, the influence of the pulsation can be removed by averaging the two values. Also, the two output corresponding values Ipr1-6 and Ipr1-8 are presumed to be a value containing noise and a value erroneously detected by the mounted oxygen sensor 20, respectively. However, since both the values fall outside the range R1, they are not used for calculation of the average output value Ipav, and are discarded (S14).

Subsequently, in S12, the CPU 2 performs processing of obtaining the weighted average of a plurality of output corresponding values Ipr (specifically, processing of obtaining the weighted average of 128 output corresponding values Ipr) in accordance with the following Eq. 1, for example. The weighted average of the output corresponding values Ipr severs as a weighted average Ipav which corresponds to the average output value in step S22, described below.

$$Ipav = \tfrac{1}{128} \times \{\text{latest } Ipr - Ipav(n-1)\} + Ipav(n-1) \qquad \text{(Eq. 1)}$$

Ipav(n−1) of Eq. 1 represents the weighted average calculated in the processing cycle (immediately) prior to the current processing cycle. Notably, since the value of Ipav(n−1) is not present immediately after the start of the atmospheric correction processing, the first obtained value of Ipr is substituted for Ipav(n−1) so as to obtain the weighted average Ipav. When the processing of obtaining the weighted average of the values Ipr (S12) ends, when the negative determination is made in S6 (S6: NO), or when the processing of S14 ends, the CPU 2 proceeds to S25.

Meanwhile, when the CPU 2 determines in S4 that the F/C does not continue (S4: NO), the CPU 2 changes the value of the correction flag from "1" to "0" (S16) and proceeds to S20. In S20, the CPU 2 determines, until the F/C under the specific operating conditions ends, whether or not the amount of scavenging air (the total supply amount M1 of air) cumulatively calculated in the single fuel cut period becomes equal to or greater than the predetermined amount M2 (e.g., 50 g) (S20). In the case where the total supply amount M1 has become equal to or greater than the predetermined amount M2 (e.g., 50 g) (S20: YES), the CPU 2 acquires, as Ipav (average output value), the weighted average of the output corresponding values Ipr calculated in S12 (S22). In the case where the total supply amount M1 has not yet become equal to or greater than the predetermined amount M2 (S20: NO), the CPU 2 discards the weighted average (S24) because the number of the output corresponding values Ipr used in the calculation of the weighted average (S12) is not sufficient.

Upon completing the processing of S22, the CPU 2 declares to execute the Ipavf acquisition processing of obtaining a plural-time average output value Ipavf (S23). Upon completing the processing of S23 or S24, the CPU 2 proceeds to S25. In S25, the CPU 2 determines whether or not it has declared in S23 to execute Ipavf acquisition processing. In the case where the CPU 2 has declared to execute Ipavf acquisition processing (S25: YES), the CPU 2 proceeds to S26. In the case where the CPU 2 has not yet declared to execute Ipavf acquisition processing (S25: NO), the CPU 2 ends the processing. In S26, the CPU 2 determines whether or not the average output value Ipav used for calculation of the correction coefficient Kq falls within a predetermined second range R2. In the case where the CPU 2 determines in S26 that the average output value Ipav falls within the second range R2 (S26: YES), the CPU 2 proceeds to S28.

Figure 4:
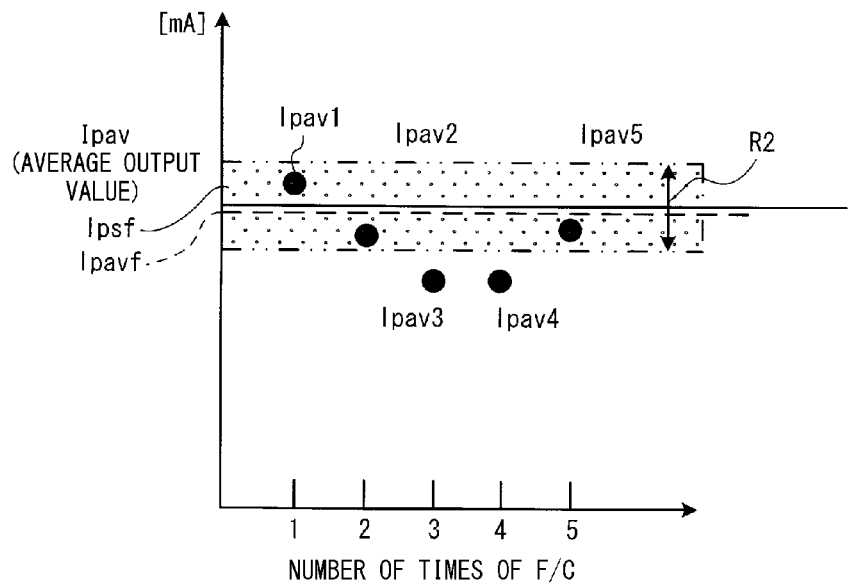
FIG. 4 is a chart showing a method for calculating a plural-time average output value Ipavf by averaging actual output values Ipav each obtained for a single fuel cut operation by the method shown in FIG. 3.

Even in the case where the F/C is repeatedly performed under the specific operating conditions, as shown in FIG. 4, a variation may arise among the individual weighted averages (Ipav1, Ipav2, etc.) obtained by the processing of S22 due to a variation (deviation) in the operation state of the internal combustion engine 100. In view of this, of the individual weighted averages (Ipav1, Ipav2, etc.), only those values which fall within the predetermined second range R2 are obtained and used for calculating the plural-time average output value Ipavf. Thus, the plural-time average output value Ipavf can be calculated such that it becomes a stable value. Notably, the upper and lower limits of the range R2 are determined on the basis of the fuel-cut reference output value Ipsf and a predetermined variation range. For example, the upper limit is set to a value obtained by adding 2% of the fuel-cut reference output value Ipsf to the fuel-cut reference output value Ipsf (center value), and the lower limit is set to a value obtained by subtracting 2% of the fuel-cut reference output value Ipsf from the fuel-cut reference output value Ipsf (center value). In this case, as shown in FIG. 4, since both the two weighted averages Ipav3 and Ipav4 fall outside the range R2, they are not used for calculating the plural-time average output value Ipavf (S26: NO).

Notably, since the range R2 is applied to the average output value Ipav whose pulsation has been removed by averaging within the range R1, the range R2 is set such that the range R2 falls within the range R1 (R2<R1). By setting the range R2 to satisfy the relation R2<R1, the plural-time average output value Ipavf can be calculated while average output values Ipav involving errors are eliminated. Thus, the reliability of the calculated plural-time average output value Ipavf is improved.

In the case where the CPU 2 determines in S26 that the average output value Ipav falls within the second range R2 (S26: YES), the CPU 2 performs the processing of obtaining the weighted average of a plurality of weighted averages Ipav (specifically, the processing of obtaining the weighted average of 16 weighted averages Ipav) (S28). This processing is performed in accordance with the following Eq. 2, for example, and the weighted average of the weighted averages Ipav is obtained as a plural-time average output value Ipavf (S28).

$$Ipavf = 1/16 \times \{\text{latest } Ipav - Ipavf(n-1)\} + Ipavf(n-1) \quad \text{(Eq. 2)}$$

Ipavf(n−1) of Eq. 2 represents the weighted average calculated in the processing cycle (immediately) prior to the current processing cycle. Notably, since the value of Ipavf(n−1) is not present immediately after the start of the atmospheric correction processing, the first obtained value of Ipav is substituted for Ipavf(n−1) so as to obtain the weighted average Ipavf.

Meanwhile, in the case where the weighted average Ipav falls outside of the range R2 (S26: NO), the CPU 2 proceeds to S30 so as to determine whether or not the number of times the weighted average Ipav has fallen outside of the range R2 (S26: NO) exceeds a predetermined number of times (S30). The processing of S30 corresponds to, for example, an operation of counting the number of the weighted averages (Ipav3, Ipav4) having deviated from the range R2 in FIG. 4. In the case where the number of times the weighted average Ipav has fallen outside of the range R2 exceeds the predetermined number of times (S30: YES), the CPU 2 determines that the mounted oxygen sensor 20 has frequently output anomalous values, instructs replacement of the sensor (S32), and ends the present processing. The CPU 2 can provide the sensor replacement instruction to a driver of the vehicle by, for example, providing a warning to the driver or displaying a message which urges the driver to replace the sensor. Meanwhile, in the case where the number of times the weighted average Ipav has fallen outside of the range R2 (S26: NO) does not exceed the predetermined number of times (S30: NO), the CPU 2 ends the present processing.

Figure 5:
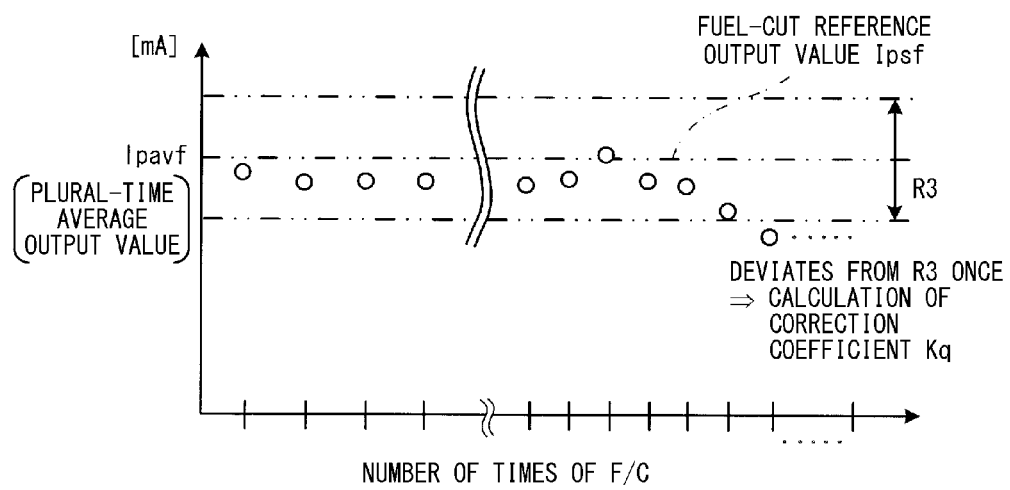
FIG. 5 is a chart showing a method for determining whether or not the plural-time average output value Ipavf obtained by the method shown in FIG. 4 has deviated from a range R3, which is a correction determination range.

Subsequently, upon completing the processing of S28, the CPU 2 determines whether or not the plural-time average output value Ipavf obtained in S28 falls within a predetermined third range R3 (S36). As shown in FIG. 5, the upper and lower limits of the range R3 are determined on the basis of the fuel-cut reference output value Ipsf and a predetermined variation range. For example, the upper limit is set to a value obtained by adding 1% of the fuel-cut reference output value Ipsf to the fuel-cut reference output value Ipsf (center value), and the lower limit is set to a value obtained by subtracting 1% of the fuel-cut reference output value Ipsf from the fuel-cut reference output value Ipsf (center value). Notably, since the range R3 is used so as to determine whether to update the correction coefficient Kq in each F/C, the range R3 is set such that the range R3 falls within the range R2 (R3<R2).

If the plural-time average output value Ipavf falls outside the third range (even one time) (S36: NO), the CPU 2 proceeds to S40, and executes the processing of calculating a new correction coefficient Kq (S40). In S40, the CPU 2 calculates the correction coefficient Kq by dividing the fuel-cut reference output value Ipsf stored in the nonvolatile memory 8 by a value obtained by dividing the latest plural-time average output value Ipavf (i.e., the plural-time average output value Ipavf having deviated from the range R3) by the current correction coefficient Kp.

$Kq$=the fuel-cut reference output value $Ipsf$/(the latest plural-time average output value $Ipavf$/the current correction coefficient $Kp$)

Then, the CPU 2 executes processing of storing the correction coefficient Kq calculated in S40 in the nonvolatile memory 8 as a new correction coefficient Kp for the purpose of update (overwriting) (S42). By virtue of this processing, the actual output value Ip which is output from the mounted oxygen sensor 20 after that point is corrected by the new correction coefficient Kp so as to calculate the output corresponding value Ipr, and the concentration of oxygen contained in exhaust gas is determined from this output corresponding value Ipr.

Meanwhile, in the case where the CPU 2 makes a "YES" determination in S36, the CPU 2 ends the present processing. That is, the latest correction coefficient Kp is used without being updated.

As described above, in the oxygen sensor control apparatus 10 of the present embodiment, from a plurality of output corresponding values Ipr of the mounted oxygen sensor 20 obtained during a single fuel cut period, those deviating from the first range R1 are removed, and the remaining values Ipr are used so as to calculate the average output value Ipav. The calculated average output value Ipav is used for calculating the plural-time average output value Ipavf. Moreover, a new correction coefficient Kq is obtained for the purpose of update, through comparison between the plural-time average output value Ipavf and the fuel-cut reference output value Ipsf. Thus, in the oxygen sensor control apparatus 10 of the present embodiment, the relation between the output of the oxygen sensor (the mounted oxygen sensor 20) and oxygen concentration can be calibrated accurately, and detection of the oxygen concentration can be continued by use of the accurate correction coefficient. Thus, the detection accuracy of the oxygen sensor can be maintained at a satisfactory level for a long period of time.

Notably, in the present embodiment, the CPU 2 which executes the processing of S40 is an example of the "correction coefficient calculation means;" and the CPU 2 which executes the processing of S10 and S12 is an example of the "average output value calculation means." Also, the CPU 2 which executes the processing of S26 and S28 is an example of the "plural-time average output value calculation means;" Ipav is an example of the "average output value;" and Ipavf is an example of the "plural-time average output value." The RAM 4 which cumulatively stores the total supply amount M1 is an example of the "total supply amount calculation means;" and the CPU 2 which executes the processing of S6 is an example of the "total supply amount determination means."

Notably, the present invention is not limited to the above-described embodiment, and various modifications are possible. For example, the mounted oxygen sensor 20 is not limited to a two-cell-type air-fuel-ratio sensor, and may be a one-cell-type limiting-current air-fuel-ratio sensor. Furthermore, in the above-described embodiment, each of the average output value Ipav and the plural-time average output value Ipavf is obtained as a weighted average. However, instead of the weighted average, an arithmetic average or moving average of relevant values may be used.

In the above-described embodiment, the determination as to whether a value falls within the first range R1 is performed for the output corresponding value Ipr, which is obtained by multiplying the actual output value Ip of the mounted oxygen sensor 20 by the correction coefficient Kp. However, the embodiment may be modified such that the first range (numerical range) R1 is properly changed, the actual output value Ip is compared with the changed first range R1 so as to exclude the values deviating from the first range R1, and the average of the remaining values is multiplied by the correction coefficient Kp so as to obtain the average output value Ipav. In the above-described embodiment, the predetermined amount used in the steps S6 and S20 is a fixed value (M2). However, the predetermined amount may be a variable value which changes in accordance with, for example, the engine rotational speed immediately before the F/C is started under the specific operating conditions. Moreover, instead of using the same predetermined amount in the steps S6 and S20, the predetermined amount used in the step S20 may be set to be greater than the predetermined amount used in the step S6 so as to acquire the weighted average as Ipav when the F/C continues for a certain period of time after the total supply amount M1 has reached the predetermined amount of the step S6.

The invention has been described in detail with reference to the above embodiments. However, the invention should not be construed as being limited thereto. It should further be apparent to those skilled in the art that various changes in form and detail of the invention as shown and described above may be made. It is intended that such changes be included within the spirit and scope of the claims appended hereto.

This application is based on Japanese Patent Application No. JP 2011-141261 filed Jun. 24, 2011, incorporated herein by reference in its entirety.

What is claimed is:

1. An oxygen sensor control apparatus which obtains a correction coefficient when a fuel cut operation is performed so as to stop the supply of fuel to an internal combustion engine, the correction coefficient being used to calibrate the relation between an actual output value of an oxygen sensor attached to an exhaust pipe of the internal combustion engine and the oxygen concentration, and which detects the oxygen concentration of the exhaust gas through use of the actual output value and the correction coefficient, the oxygen sensor control apparatus comprising:

average output value calculation means for calculating an average output value by averaging a plurality of actual output values of the oxygen sensor acquired in each period in which the fuel cut operation is performed once or by averaging concentration corresponding values calculated from the actual output values and representing the oxygen concentration acquired in each period in which the fuel cut operation is performed once;

plural-time average output value calculation means for calculating a plural-time average output value for performance of the fuel cut operation in a predetermined number of times equal or greater than two times, by averaging a plurality of the average output values each calculated for each performance of the fuel cut operation;

correction coefficient calculation means for obtaining a new correction coefficient on the basis of the plural-time average output value and a reference output value set in advance, the new correction coefficient being used for correcting the actual output value of the oxygen sensor;

total supply amount calculation means for acquiring, from supply amount measurement means for measuring the amount of air supplied from the internal combustion engine to the exhaust pipe, the amount of air supplied to the exhaust pipe, and for calculating a total supply amount, which is the total amount of air supplied to the exhaust pipe during each period in which the fuel cut operation is performed once; and total supply amount determination means for determining, in each period in which the fuel cut operation is performed once, whether or not the total supply amount calculated by the total supply amount calculation means becomes equal to or greater than a predetermined amount set in advance, wherein the average output value calculation means calculates the average output value from a plurality of the actual output values of the oxygen sensor or the concentration corresponding values acquired at predetermined time intervals after the total supply amount determination means determines that the total supply amount from the start of the fuel cut operation becomes equal to or greater than the predetermined amount.

2. The oxygen sensor control apparatus as claimed in claim 1, wherein the average output value calculation means removes values deviating from a first range from a plurality of actual output values of the oxygen sensor acquired in each period in which the fuel cut operation is performed once or form the concentration corresponding values calculated from the actual output values and representing the oxygen concentration acquired in each period in which the fuel cut operation is performed once, and calculates the average output value by averaging the remaining values.

3. The oxygen sensor control apparatus as claimed in claim 2, wherein the first range is set around the reference output value such that the center of the first range coincides with the reference output value.

* * * * *